(12) United States Patent
Mensa

(10) Patent No.: US 10,578,508 B2
(45) Date of Patent: Mar. 3, 2020

(54) ELECTRO-MECHANICAL MINIATURIZED DEVICE FOR PRESSURE MEASUREMENTS

(71) Applicant: NANOTECH ANALYSIS S.R.L., Turin (IT)

(72) Inventor: Gianpiero Mensa, Turin (IT)

(73) Assignee: NANOTECH ANALYSIS S.R.L., Turin (IT)

(*) Notice: Subject to any disclaimer, the term of this patent is extended or adjusted under 35 U.S.C. 154(b) by 47 days.

(21) Appl. No.: 15/114,621

(22) PCT Filed: Jan. 29, 2015

(86) PCT No.: PCT/IB2015/050673
§ 371 (c)(1),
(2) Date: Jul. 27, 2016

(87) PCT Pub. No.: WO2015/114553
PCT Pub. Date: Aug. 6, 2015

(65) Prior Publication Data
US 2016/0341622 A1  Nov. 24, 2016

(30) Foreign Application Priority Data
Jan. 31, 2014  (IT) .............................. MI2014A0141

(51) Int. Cl.
*G01L 27/00* (2006.01)
*B81B 3/00* (2006.01)
*G01L 9/00* (2006.01)

(52) U.S. Cl.
CPC .......... *G01L 27/002* (2013.01); *B81B 3/0021* (2013.01); *G01L 9/0008* (2013.01); *B81B 2201/0264* (2013.01)

(58) Field of Classification Search
CPC ... G01L 9/0008; G01L 9/0019; G01L 9/0022; G01L 9/12; G01L 15/00; G01L 27/002; B81B 3/0021
(Continued)

(56) References Cited
U.S. PATENT DOCUMENTS 6,051,853 A * 4/2000 Shimada ............... G01L 9/0042
257/248
2005/0130360 A1* 6/2005 Zhan ..................... B81B 3/0021
438/197
(Continued)

FOREIGN PATENT DOCUMENTS

CN  101490521 A  7/2009
CN  103308239 A  9/2013
(Continued)

OTHER PUBLICATIONS

International Search Report for PCT/IB2015/050673, dated May 4, 2015.
Written Opinion for for PCT/IB2015/050673, dated May 4, 2015.

*Primary Examiner* — Benjamin R Schmitt
(74) *Attorney, Agent, or Firm* — Arent Fox LLP; Michael Fainberg

(57) ABSTRACT

An electro-mechanical miniaturized device for pressure measurements is described, the device comprising at least one first electro-mechanical miniaturized pressure sensor member, configured to detect a respective first pressure value P1 and to generate a first electrical signal S1 representative of the first pressure value P1, and further comprising at least one second electro-mechanical miniaturized pressure sensor member, configured to detect a respective second pressure value P2 and to generate a second electrical signal S2 representative of said second pressure value P2. The second sensor member is arranged within a casing suitable to seal it. The device further comprises electronic
(Continued)

processing means, operatively connected to the first and the second sensor members, and configured to determine a measured pressure value P based on said first S1 and second S2 electrical signals.

15 Claims, 6 Drawing Sheets

(58) Field of Classification Search
USPC .................................. 73/1.57, 1.63, 753, 754
See application file for complete search history.

(56) References Cited

U.S. PATENT DOCUMENTS

| 2006/0288573 | A1* | 12/2006 | Aizawa | G01L 9/0042 |
| | | | | 29/846 |
| 2007/0125161 | A1* | 6/2007 | Bryzek | B60C 23/0408 |
| | | | | 73/146.4 |
| 2010/0024517 | A1 | 2/2010 | Ratner | |
| 2010/0083764 | A1* | 4/2010 | Kurtz | G01L 9/0054 |
| | | | | 73/721 |
| 2011/0239772 | A1 | 10/2011 | Kurtz et al. | |

FOREIGN PATENT DOCUMENTS

| EP | 1571435 | A1 | 9/2005 |
| EP | 2330396 | A1 | 6/2011 |

\* cited by examiner

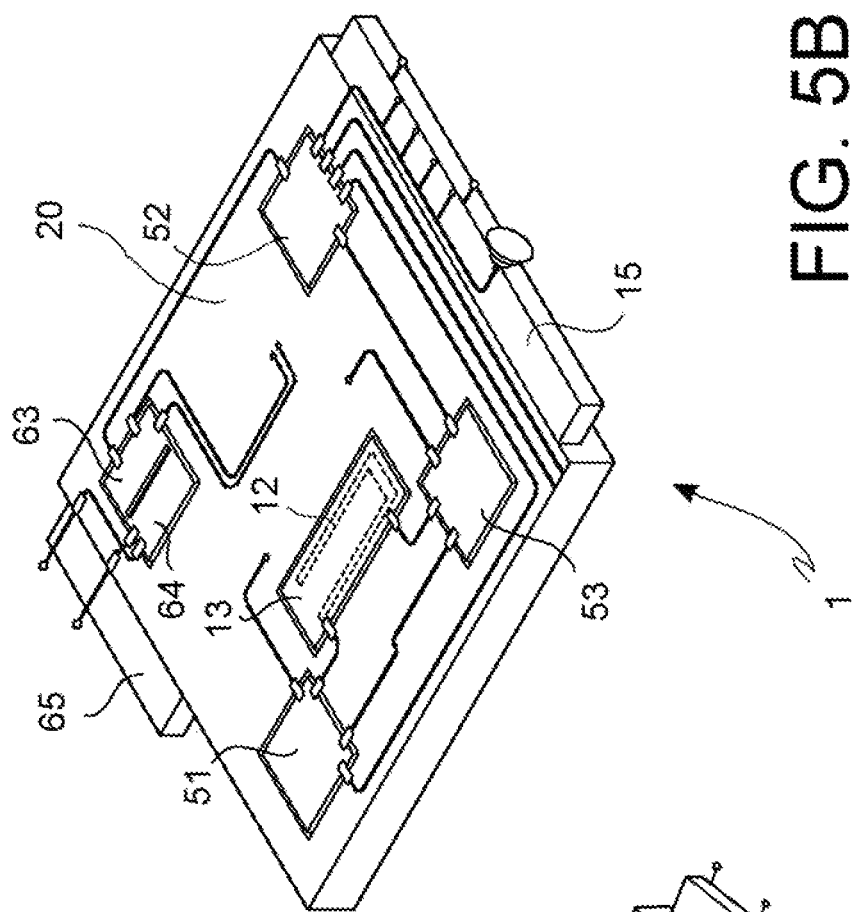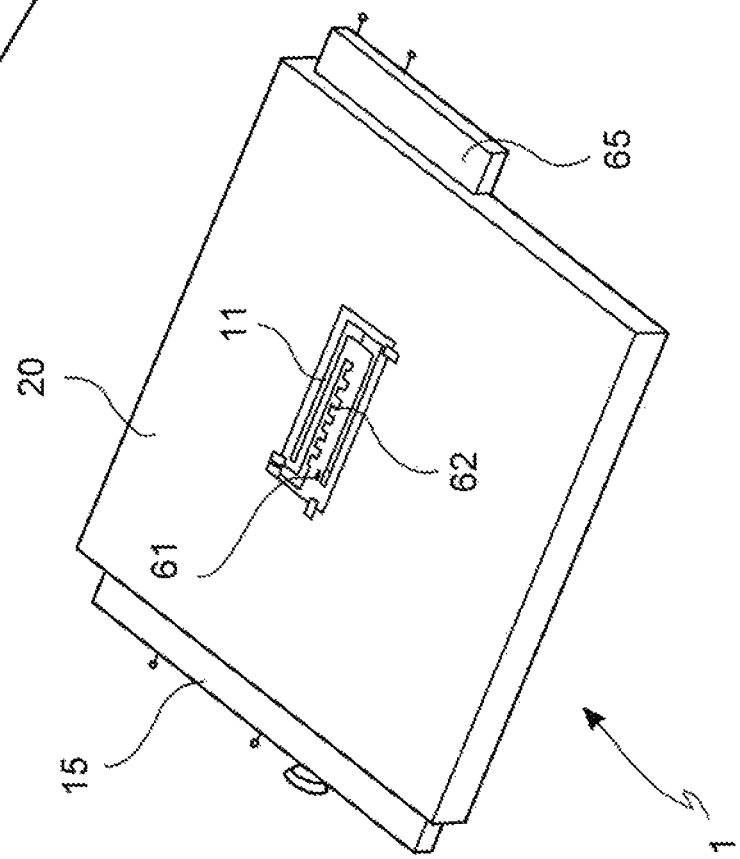

ELECTRO-MECHANICAL MINIATURIZED DEVICE FOR PRESSURE MEASUREMENTS

TECHNOLOGICAL BACKGROUND OF THE INVENTION

Field of Application

The present invention relates to the field of pressure sensor devices, particularly miniaturized electro-mechanical sensor devices, for use to measure pressures over a wide range (from overpressures but with the exception of high vacuum conditions), for example in machines, plants or instruments for measurements and analyses.

Background

Several electro-mechanical systems and devices for measurements of pressure are known.

A first category of devices comprises devices of the Pirani or thermo-cross type or devices of the MacLeod type, which are however considered as "low-end" devices, in terms of performance and measurement precision. Therefore, these devices cannot be used for many applications that require high precision and wider measurement ranges.

A second category of devices comprises diaphragm capacitive pressure sensors, which are considered "high-end" devices, in terms of performance and measurement precision. However, a first drawback of these capacitive pressure sensors is the range of measurable pressures, that is rather narrow for a given device. Therefore, in order to measure a pressure over a wide range of pressures, multiple pressure sensors have to be used in parallel: for example at least three capacitive pressure sensors in parallel are typically required for measurements over a pressures range between $10^{-4}$ mbar and $10^3$ mbar, and no commercial instruments capable to measure pressures ranging from $10^{-4}$ mbar to $10^4$ mbar are known Moreover, in order to work efficiently in a real operating environment, the individual pressure measurement devices must include not only the pressure sensor itself, but also further components (for example, processing modules, interface modules, either wired or wireless, towards higher-level controllers, etc.). Thus, each of these devices becomes a "system", even though of small dimensions. Disadvantageously, this reduces the reliability and increases the complexity of the devices, also increasing design and maintenance costs.

It should be further noted that a field of application, having a great and growing importance, is related to the use of pressure measurement systems/devices inside production machines or plants or manufacturing environments or analysis and measurement instruments, where it may be necessary to measure the pressure with a high precision, in many different points, over wide ranges, in often unfavorable environmental conditions, resulting in critical, or even extreme, operating conditions for the devices.

In this field of application, the need arises to have devices as compact, simple and miniaturized as possible, while maintaining high performance in terms of precision and reliability, and also significantly reducing the production and management costs thereof.

The known cited devices, both the "low-end" ones and the "high-end" ones, do not comply to this need in a satisfactory way.

In addition to the above, with reference to the properties of precision and reliability, calibration procedures, before use, and diagnostics procedures, during use, with possible re-adjustment or re-calibration, are more and more important.

Regarding this, the existing solutions do not offer a solution, or, at the most, they allow performing remote control procedures, by means of high level system controllers, which manage, for example, a plurality of devices in a plant. These control procedures may be complex and costly, in terms of time and resources needed.

More specifically, when compared with the requirements of the above-mentioned applications, the known sensor devices may have several drawbacks, among which: the non-perfect repeatability of pressure measurements, for example during pressure cycles of an industrial process; the existence of severe limitations of use in applications providing the exposure to corrosive gases environments; the difficulty of use in environments having abundant soot and particulate; the need to extract the device, from the system where it works, for calibration or re-calibration or cleaning, every time a new process cycle starts; finally, the need for a complex and cumbersome management and measurement system to obtain a microscopic measurement signal using macroscopic measurement and management instruments of the device.

Therefore, the further need of having pressure measurement devices as "self-contained" as possible, with respect to calibration and diagnostics, is much felt. Again, the known devices cited above do not offer suitable fulfillments to this need.

It should also be observed that the needs for miniaturization and self-sufficiency, even if they are both desired, may put conflicting design requirements which are very difficult to fulfill altogether.

In light of the above, the object of the present invention is to devise and provide a miniaturized electro-mechanical device for pressure measurements over a wide range (and a related measurement method), which results to be improved such as to fulfill the above-mentioned needs, and to be able to at least partially overcome the drawbacks described above with reference to the prior art.

SUMMARY OF THE INVENTION

This object is achieved by a device according to claim 1.

Further embodiments of this device are defined in the dependent claims 2 to 13.

A method for measuring pressure, carried out by the device of the invention, is defined in claim 14.

A further embodiment of the method is defined in claim 15.

BRIEF DESCRIPTION OF THE DRAWINGS

Further characteristics and advantages of a miniaturized device for pressure measurements, according to the present invention, will result from the following description of preferred exemplary embodiments given by way of indicative and non-limiting examples, with reference to the attached figures, in which:

FIGS. 5A and 5B illustrate a structural diagram of a second embodiment of a device according to the invention;

DETAILED DESCRIPTION

Figure 1:
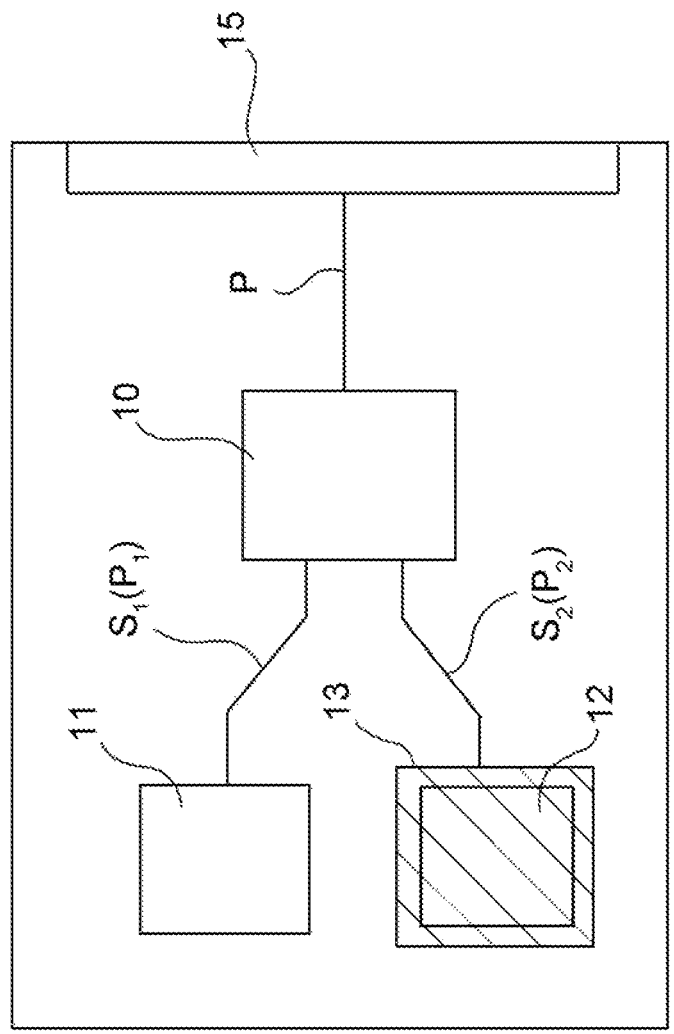
FIG. 1 illustrates a simplified functional diagram of the device according to the invention.
Figure 2:
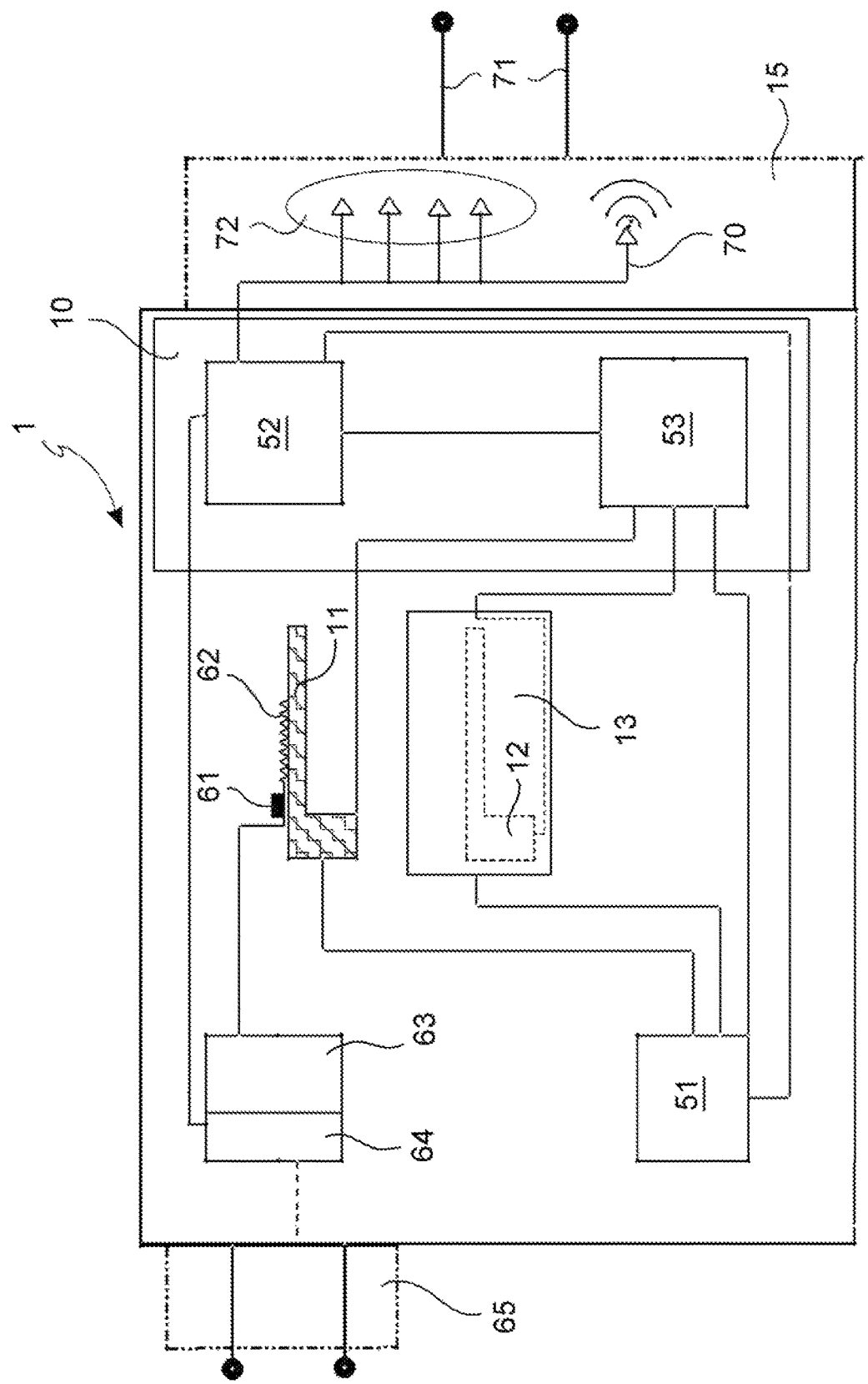
FIG. 2 illustrates a more detailed schematic diagram of an exemplary embodiment of the device according to the invention.

With reference to FIGS. 1-6, an electro-mechanical miniaturized device 1 for pressure measurements, according to the invention, is described.

This device 1 comprises at least one first electro-mechanical miniaturized pressure sensor member 11, configured to detect a first pressure value $P_1$ and to generate a first electrical signal $S_1$ representative of the above-mentioned first pressure value $P_1$.

The device 1 also comprises at least one second electro-mechanical miniaturized pressure sensor member 12, configured to detect a respective second pressure value $P_2$ and to generate a second electrical signal $S_2$ representative of the above-mentioned second pressure value $P_2$.

The second electro-mechanical miniaturized pressure sensor member 12 is arranged within a respective casing 13 suitable to seal the second sensor member.

The device 1 then comprises electronic processing means 10, which are operatively connected to the first and second sensor members (11 and 12, respectively) and are configured to determine a measured pressure value P based on the first and second electrical signals (respectively, $S_1$ and $S_2$), generated by the sensor members 11, 12, and received by the electronic processing means 10.

The device 1 also comprises interface means 15, operatively connected to the electronic processing means 10, and configured to provide in output the above-mentioned measured pressure value P.

The at least one first sensor member 11, the at least one second sensor member 12, the electronic processing means 10 and the interface means 15 are all included in a single integrated device.

It should be noted that as "integrated device" is meant herein a device that is manufactured by means of integrated micro/nano-electronic techniques and that is contained, or containable in a single, individual package.

According to a preferred exemplary embodiment, the device 1 is an integrated device made by means of a single chip 20 (shown for example in FIG. 3), typically made of silicon. In this case, the first and second sensor members, the electronic processing means and the interface means are all included, i.e., integrated, in the chip 20 of the integrated device 1.

According to a different example, also included in the invention, the device 1 comprises two half-chips, which are connected to each other also at a microscopic level.

According to other exemplary embodiments, the device 1 may comprise multiple chips connected to each other at a microscopic scale, or an individual multi-layer chip, such as to obtain anyway an integrated device.

Based on the above, the definition of "miniaturized device" can be also understood, i.e., a device which, being integrated, has a size in the micrometric scale, for example of an overall order of magnitude of hundreds of $\mu m^2$ or of $mm^2$, which size is still lower than the minimum size that can be handled and operated, wherein such minimum size is obtained by providing the device with a suitable packaging.

It should be further noted that such a miniaturization not only concerns the actual sensor members (which allows the measurement range to be extended) but also the further processing and interface members belonging to the device (which contributes to improve the signal-to-noise ratio).

Now, with reference to the first and second sensor members, it should be noted that they can be implemented, in principle, by means of any electro-mechanical transducer able to provide an electrical variable representing the detected pressure.

Particularly, the first 11 and second 12 sensor members are configured to have a mechanical or electro-mechanical behaviour, respectively correlated to a first and to a second mechanical or electro-mechanical variable (for example, position, or movement, or oscillation) depending on the pressure ($P_1$, $P_2$, respectively) or on the fluid-dynamics to which the sensor members are respectively subjected.

Moreover, the first 11 and second 12 sensor members are further configured to either generate or transform the above-mentioned first $S_1$ and second electrical signal $S_2$ (representative of the first and second pressure values $P_1$ and $P_2$, respectively) based on the respective first and second mechanical or electro-mechanical variables that are sensible to pressure or to fluid-dynamics.

For example, the amplitude or resonance frequency or width of the spectrum peak or other electrical variables of the electrical signals $S_1$ and $S_2$ can be correlated and can represent (according to per-se known theoretical perspectives) a pressure value detected by the respective sensor member.

It should be noted that the two sensor members, in a preferred exemplary embodiment, are identical, and are designed to behave in the same way, based on the same principles and on the same variables.

In other exemplary embodiments, the two sensor members can even differ from each other, as long as the correlation of their behaviours is precisely known, such as to allow to define a "nominal behaviour" and, as it will be better explained herein below, to identify possible deviations of the first sensor member 11 from such "nominal behaviour".

Now with reference to FIGS. 2-6, a device according to a preferred exemplary embodiment (and related variations/options) is better illustrated, where the first 11 and second 12 sensor members are similar to each other, and each of them comprises a respective oscillating member of the MEMS/NEMS (Micro/Nano-Electro-Mechanical System) type.

Particularly, according to an embodiment, such MEMS/NEMS-type oscillating member comprises a micro-cantilever configured to oscillate with a dynamic response depending on the pressure to which it is subjected.

Therefore, in FIGS. 2-6, a first micro-cantilever, that is the first sensor member, is designated as 11, while a second micro-cantilever, that is the second sensor member, is designated as 12; the second micro-cantilever is represented in a dashed line, because it is actually covered by the casing 13, in the illustrated views.

The micro-cantilever operating principle provides that the characterizing electro-mechanical variable is related to the oscillation: the micro-cantilever oscillates with a frequency damping with a damping factor $\alpha$ depending on the pressure to which it is subjected. Therefore, it is able to generate an electrical signal (i.e. $S_1$ or $S_2$) whose dynamic response is representative of the pressure to which the micro-cantilever is subjected. Typically, the damping factor $\alpha$ is inversely proportional to the thickness d of the micro-cantilever. Therefore, the miniaturization of the micro-cantilever (and, generally speaking, of the sensor member) is an important aspect in order to allow the device of the invention to perform measures over a whole pressure value range that is especially wide.

According to an embodiment, each of the two micro-cantilever 11, 12 is excited by applying a forcing waveform having a known frequency. The dynamic response and, accordingly, the related typical parameters, like for example resonance frequency, Q factor, oscillation amplitude, depend on pressure. For this purpose, the device may further comprise a function generator circuit or frequency generator 51, configured to cause an input oscillation at each of the first and second micro-cantilevers, by means of an excitation signal.

Moreover, in this option, it is provided that the electronic processing means 10 comprise a processing unit 52 and a demodulating circuit 53, configured to estimate first and second output oscillation frequencies of the first and second micro-cantilevers, respectively, based on the frequency of the first electrical signal $S_1$ or of the reference electrical signal $S_2$, respectively, and of the excitation signal; the demodulating circuit 53 then communicates to the processing unit 52 an information related to these first and second oscillation frequencies and excitation signal frequency.

According to an exemplary embodiment, as shown in the figures, this demodulating circuit 53 is a signal lock-in circuit.

The embodiment illustrated above is actually based on a double MEMS/NEMS oscillator, integrated in the device, where the two MEMS/NEMS oscillators share the frequency generation and demodulation lock-in circuit, and are instead characterized by the first and second micro-cantilevers, as the respective active member.

The frequency generation circuit 51 "excites" both micro-cantilevers, and the lock-in circuit 53 detects the output oscillation frequencies of both micro-cantilevers 11, 12, thereby providing a signal depending on the comparison of these two output frequencies with the reference excitation signal(s).

By considering the device as comprising a double MEMS/NEMS oscillator, it can be understood how a plurality of pressure detection methodologies can be applied. Actually, the device can be configured to detect the pressure based on one or more characteristics of the electrical signals $S_1$ and $S_2$: for example, based on a variation of the oscillation frequency relative to a nominal (or forcing) frequency; or based on a broadening of the oscillation peak, as visible in the spectrum of each electrical signal; or by measuring its Q factor. To this end, it is possible to use, for example, known methodologies and correlations for the operation of micro-cantilever oscillators, among which those reported in Hosaka et al., "*Damping characteristics of beam-shaped micro-oscillators*", Sensors and Actuators A 49 (1995), 87-95, may be cited for example.

According to a particular exemplary embodiment, the micro-cantilevers of the first and second sensor members are configured to oscillate in a parallel direction relative to the surface of the chip 20 forming the device.

According to another particular exemplary embodiment, the micro-cantilevers of the first and second sensor members are configured to oscillate in a perpendicular direction relative to the surface of the chip 20 forming the device.

With reference to the sealing and protective casing 13, it should be noted that, according to an exemplary embodiment, it is configured to adopt a closed state and an open state: in the closed state, it protects the at least one second sensor member 12 from being is directly exposed to the surrounding environment; in the open state, it allows the at least one second sensor member to be directly exposed to the surrounding environment.

The situation where the casing 13 is closed and sealed will be now considered. The casing 13 thereby encloses the reference sensor member 12, thus protecting it from degradation phenomena possibly resulting from environmental conditions, while keeping the pressure conditions fixed and stabilized on a known value (that will be herein called "reference pressure" since it is a certain and absolute reference point), which is defined a priori. Owing to this, the second sensor member 12 keeps the "nominal behaviour", for which it has been carefully characterized a priori, with a good or excellent accuracy. Thus, the second sensor member takes the important function of a "reference sensor", having a stable and anyway predictable behaviour, even during operation. By comparing the behaviour of the two sensors, it is thus possible to detect and correct possible deviations of the first sensor member 11 from its "nominal behaviour".

In greater detail, all the electro-mechanical or mechatronic properties of the second reference sensor member 12 are known, since they have been characterized a priori with respect to the reference pressure, for example, as a function of operating temperature, oscillation frequency, oscillation amplitude, and so on; and they have been further stored in a memory included in the electronic processing means 10.

From a mathematical point of view, the characterization data of the second sensor member actually define a "reference hypersurface" allowing to know exactly the mechatronic properties of the reference sensor member and the operating conditions (for example, operating temperature), based on the second electrical signal $S_2$ generated by the second sensor member 12, and being known the reference pressure to which the second sensor member 12 is subjected inside the sealed casing.

Therefore, when the processing means 10 receive an electrical signal $S_2$ from the second sensor member 12, they refer it to the known reference pressure value $P_2$, as maintained inside the sealed casing 13, and thus, based on the stored characterization data, the processing means 10 can know both the mechatronic properties and the operating conditions of the reference sensor member 12. Consequently, the processing means 10 are also able to calculate the exact conversion factor existing between $S_2$ and $P_2$ (which will be o herein designated as "second conversion factor").

It should be noted that the operating conditions of the two sensor members 11 and 12, which are very close to each other, are the same, except for the pressure. Moreover, the mechatronic properties of the two sensor members are nominally the same (if the two sensor members are exactly identical) or at least they are correlated to each other in a known and is deterministic way (if the two sensor members are not identical) depending on preset design criteria.

Thus, based on the second conversion factor, the processing means 10 are able to calculate a suitable conversion factor (which will be designated herein as "first conversion factor" or "calibration factor") to be applied to the signal $S_1$ generated by the first sensor member 11, to calculate exactly the pressure value P to which the first sensor member 11, thus the device 1, is subjected, i.e., the value to be measured.

The first and second conversion factors can be exactly the same or they can be correlated to each other in a known and deterministic manner, based on the initial characterization, and varying, e.g., as a function of the pressure range over which the device is working.

Briefly, due to the fact of receiving information from both the first 11 and the second sensor member 12, the processing means 10 are capable to estimate more accurately the actual pressure present at the device, i.e., the measured pressure P, by taking into account both the first and the second electrical signals. The methodologies of estimate of the pressure P, based on the electrical signals $S_1$ and $S_2$ representative of the pressures $P_1$ e $P_2$ detected by the first 11 and by the second sensor member 12, can be various, also different from what described above by way of example.

It should be also noted that, according to an implementation option, the device comprises a plurality of second sensor members 12, in order to detect a respective plurality of second pressure values $P_2$, and generate a respective plurality of second electrical signals $S_2$ representative of such second pressure values $P_2$; the electronic processing means 10 are further configured to generate the measured pressure value P based on a processing of said second electrical signals $S_2$. The plurality of "reference sensors" can be exploited both to improve the estimate precision, along the whole measurement range of the device, and for the sake of redundancy and reliability.

The operation described above is carried out both upon activation of the device 1 and during the normal operating cycle; thus, such operation actually carries out an "initial self-calibration" and a "running calibration" procedure, which the device is able to perform.

Moreover, according to a further implementation example, the electronic processing means 10 are configured to process data received from the first 11 and second 12 sensor members and, based on such received data, to carry out a diagnostic procedure on the first sensor member 11, such as to identify potential hysteresis phenomena and/or imperfections and/or potential thermal and/or mechanical drifts which the first sensor member is subject to. More precisely, in case the pressure existing in the environment of the device is known and is equal to the reference pressure, the signals $S_1$ and $S_2$ are compared. This condition happens for example when both the environment pressure (e.g., at the end of an operating cycle) and the reference pressure are a vacuum pressure (for example UHV), maintained in the casing by means of a pressure control member ("getter"); or when the environment pressure is different from vacuum but is known, and a similar pressure is created by the "getter" in the casing 13.

In these cases, if $S_1$ and $S_2$ differ by a relatively small amount, less than a preset threshold, it means that the first sensor member 11 works well, and diagnostics have a positive outcome; possibly, the detected difference is compensated by acting on the above-mentioned first conversion factor, in a way similar to what above described about the calibration.

On the other hand, if $S_1$ and $S_2$ differ by a significant amount, for example more than the above-mentioned threshold, diagnostics have a negative outcome, and a mere calibration compensation is not sufficient anymore.

According to an implementation example, the device 1 is capable to carry out a diagnostic procedure even if the pressure of the external environment is not known, or if it does not coincide with the reference pressure. In this example, the casing 13 is temporarily opened, such as to temporarily expose the second sensor member 12 to the same environment to which the first sensor member 11 is exposed. Then, the diagnostic procedure is performed, and finally the casing 13 is closed and sealed again and the reference pressure conditions are restored, for example by means of an embedded "getter".

In case a plurality of second sensor members 12 are provided, it is possible to keep one of them always closed and sealed, under reference pressure conditions.

In case the diagnostic procedure yields a negative outcome, according to a further exemplary option, the electronic processing means 10 are also configured to carry out an adjusting and/or compensation and/or optimization procedure of the first sensor member, to correct and/or compensate hysteresis and/or imperfections and/or identified drifts, based on the results of the diagnostic procedure.

In a possible implementation option, the electronic processing means 10 are configured to store desired operating conditions of the first sensor member 11, to compare the desired operating conditions to operating conditions detected by a diagnostic procedure, and to intervene, based on such a comparison, by means of an adjustment procedure, to recover the desired operating conditions and guarantee the repeatability of the performed measurements.

The advantage of having available in the device 1 a diagnostic procedure, which is actually a "self-diagnostics", is evident. The further advantage of having available the consequent adjusting (o recalibration) procedure, which is actually a "self-adjusting" procedure, is also evident.

Only if even this "self-adjusting" procedure fails to restore proper operating conditions, a failure signal is sent from the electronic processing means 10 towards the higher level system controllers.

In order to allow the adjusting procedure, the device 1 further comprises controlled heating means, comprising one or more temperature sensors 61, e.g., miniaturized thermometer(s), and at least one heating member 62 (for example, one or more micro-resistors), placed near or over the first sensor member 11, and a heat supply (or "heater") 63, typically associated to a supply and management circuit 64 of the heating means, which is connected to an external supply interface 65. The above-mentioned controlled heating means are configured to carry out a degassing and/or a removal of gases adsorbed on the surface of the micro-cantilever 11 of the first sensor member 11, under the control of the electronic processing means 10, which in turn operate based on the temperature detected by the thermometer 61 and on the results of the diagnostic procedure.

In this case, the above-mentioned adjusting procedure of the first sensor member 11 comprises the degassing and/or removal of gases adsorbed on the surface of the micro-cantilever 11, by means of the controlled heating means.

It should be noticed that the above-mentioned heater 63 can be used to vary the operating thermal conditions of the device, in a controlled manner, also in further operating steps other than self-adjusting.

According to an exemplary embodiment, the device further comprises protection thin films, for example technical and specific films, configured to reduce the adsorption of process gases (for example hydrophobic films to prevent the adsorption of moisture present in the process environment) and to prevent corrosion phenomena. These protection thin films are arranged such as to cover at least the first sensor member 11.

According to a further exemplary embodiment, the device further comprises a package 80 comprising micrometric frame filters, and/or anti-particulate filters, arranged such as to cover at least the sensor members 11, 12, comprised in the device 1, and configured to protect them from particulate or soot. This option is particularly advantageous when the device 1 is intended to be used in industrial environments. The example described here is shown in the exploded view of FIG. 4, with reference to an embodiment of the device 1, but it can be also applied in the embodiments illustrated in FIGS. 5 and 6.

According to an implementation option, the electronic processing means 10 comprise at least one electronic processor (CPU) 52 integrated in the device 1. This CPU can then operate as an embedded on-chip programmable microprocessor.

According to an to an implementation example, the interface means 15 comprise input and output means, either wireless or wired and/or with pins. As a whole, this interface can interact with the external world (for example with an external plant control system) in a versatile and adaptable manner, both to transmit and to receive information and/or signals and/or commands.

According to an exemplary embodiment, the interface means 15 comprise both wired input means 71 and a wireless transmitter 70 (for example a WiFi transmitter), to remotely transmit signals from closed operation areas (such as tyres, pump internal zones and vacuum chambers), and output pins 72 able to provide for example a direct analog output signal and/or a digital TTL output signal and/or an interface for a serial communication protocol.

The presence of a CPU 52 and of an interface 15, integrated in the device, allows the device 1 to receive and send information (for example, control signals) from and to a higher-level control system, for example the operative control system of the plant/environment where the device operates. Thereby, the device 1 is completely integrated in the operative plant/environment.

According to an exemplary implementation option, the device 1 comprises further integrated electronic circuitry, comprising one or more of the following electronics circuits: dedicated I/O management circuits, a supply and management circuit 64 of the heating member.

Several "auxiliary" electronic circuits, optionally present in the device 1 (frequency generator 51, lock-in circuit 52, heater 53, dedicated I/O management circuits, etc.) have been illustrated above. These auxiliary electronic circuits are integrated in the device 1. Optionally, they can be made in the same chip 20 containing the sensor members 11, 12, the processing means 10 and interface means 15, or in further chips, also micro-connected to the above-mentioned main chip, such as to constitute the integrated device.

With reference to the structural aspects of the device, particularly to the case where it comprises only one chip 20, three different embodiments are illustrated in FIGS. 3, 5A-5B and 6 by way of example. These different embodiments share all the components and the structural aspects previously described, which are therefore illustrated using the same numerical references.

The embodiments differ in the way the components are arranged in the device, particularly in the single chip 20 comprised in the device.

Figure 3:
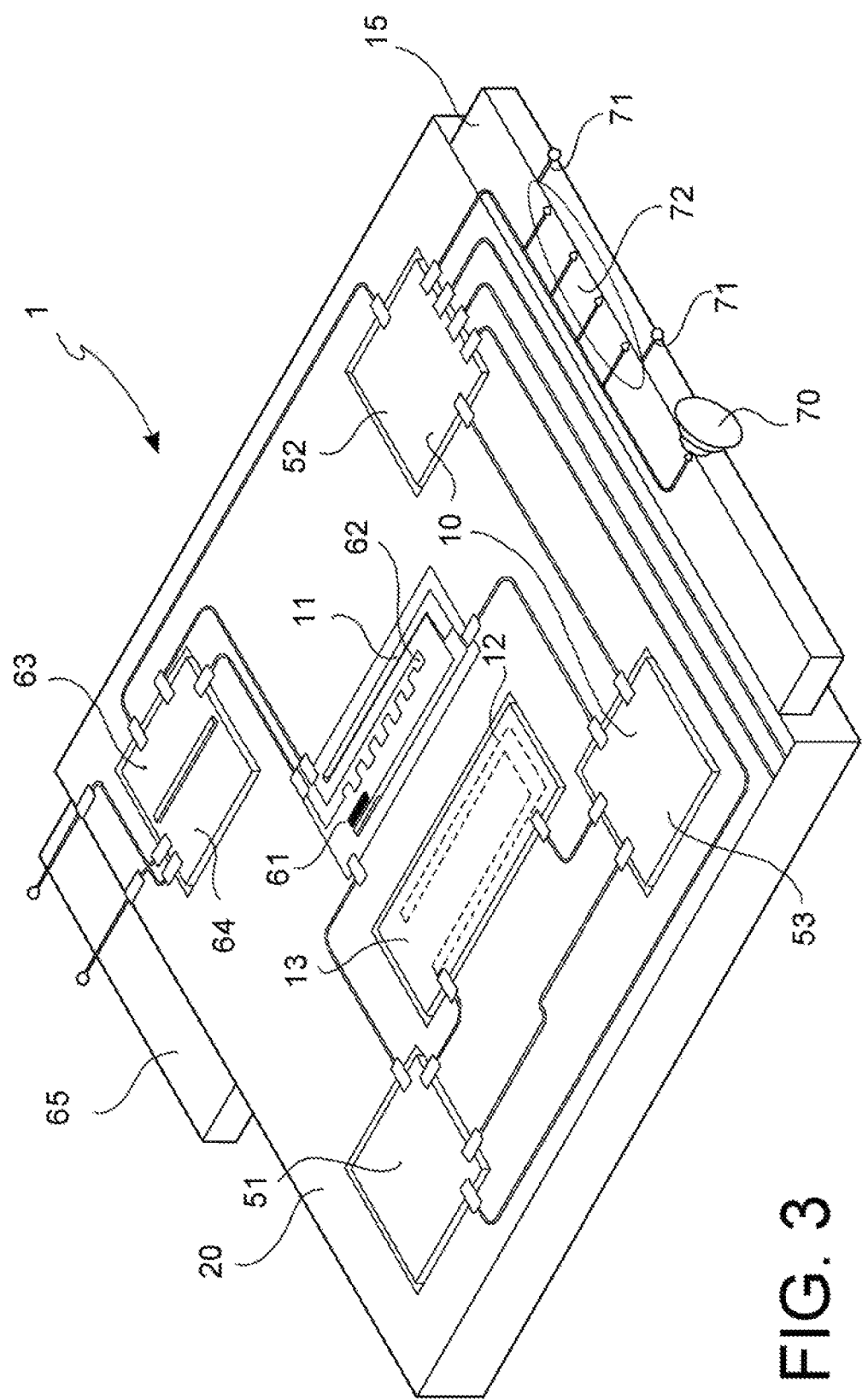
FIG. 3 illustrates a structural diagram of a first embodiment of a device according to the invention.
Figure 4:
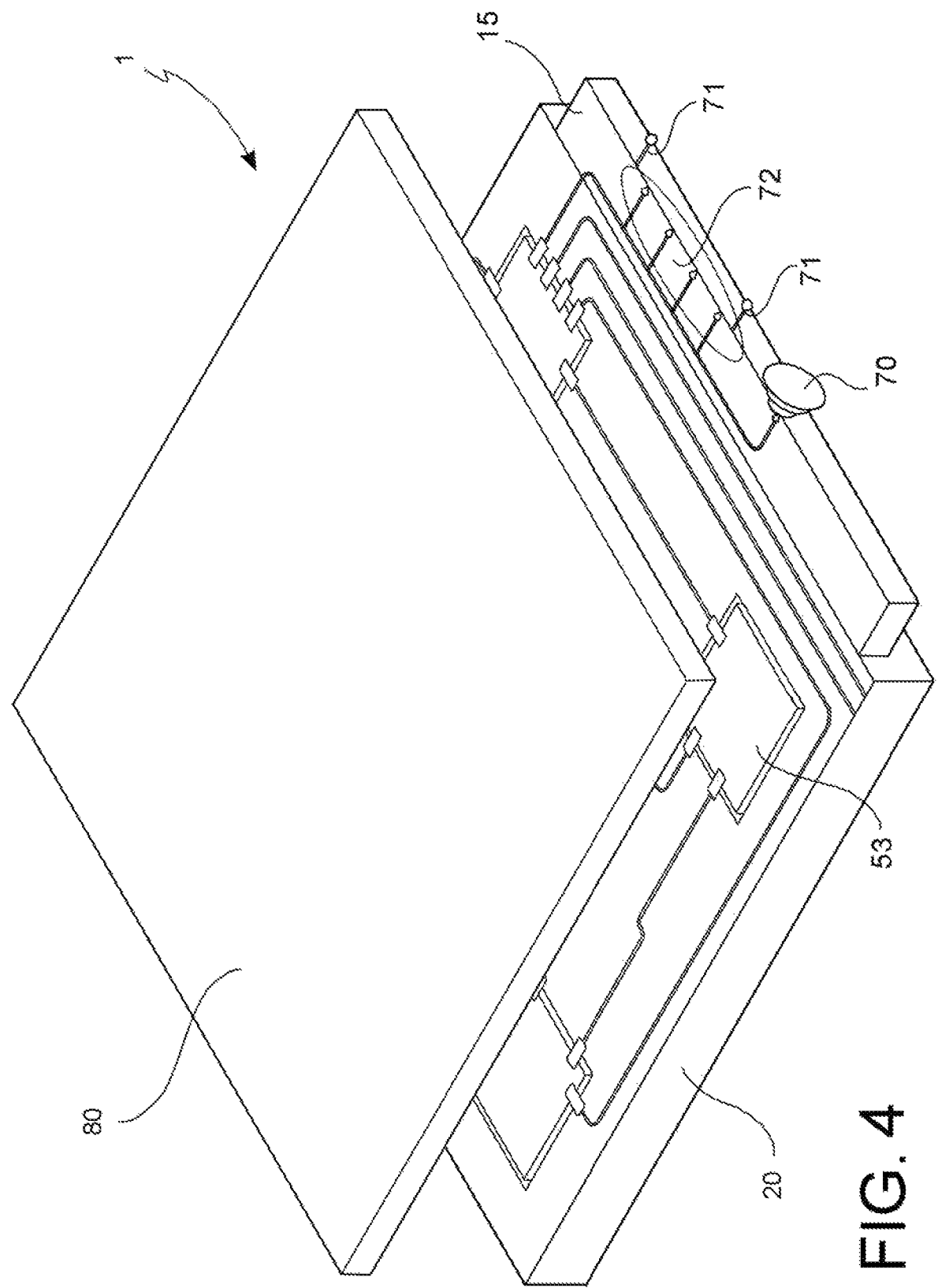
FIG. 4 is another exemplary embodiment of the device of FIG. 3.

In the first embodiment, illustrated in FIG. 3, the first 11 and second 12 sensor members and the electronic processing means 10 are arranged on the same side of the chip 20 forming the device 1.

In the second embodiment, the first 11 sensor member is arranged on one side of the chip 20, while the second sensor member 12 and the electronic processing means 10 are arranged on the other side of the chip 20 forming the device.

This is illustrated in FIG. 5A (showing one side of the chip) and 5B (showing the other side of the chip).

This second embodiment offers the advantage of segregating the heating member 62 (micro-resistor) with respect to the other components of the device, reducing the heat dissipation issues. Moreover, the other components are placed on the side of chip faced towards higher pressure or atmospheric pressure areas, such as they can be more easily cooled.

Figure 6:
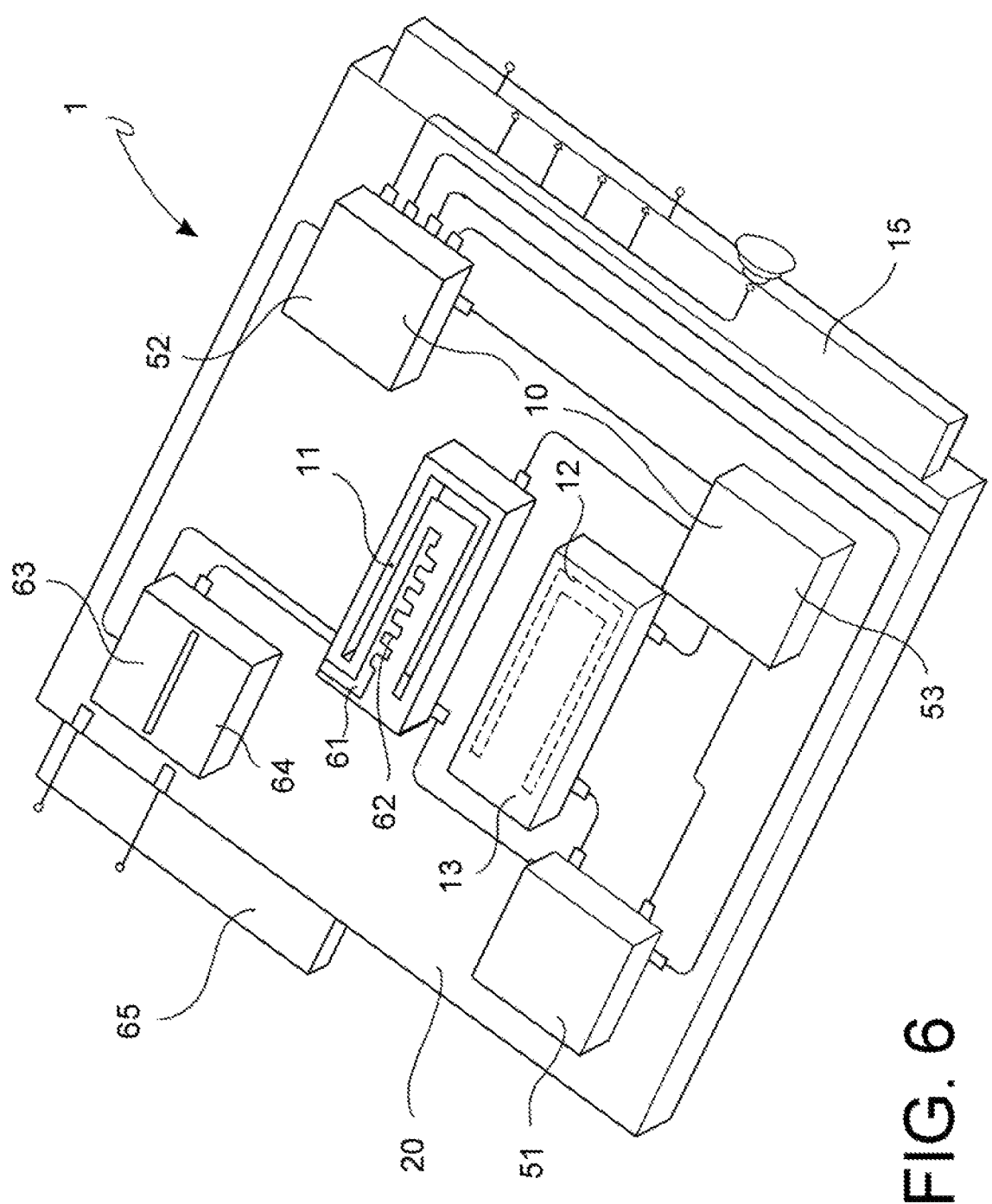
FIG. 6 illustrates a structural diagram of a third embodiment of a device according to the invention.

In the third embodiment illustrated in FIG. 6, the first 11 and second 12 sensor members and the electronic processing means 10 are arranged such as to project as a relief, on different planes, with respect to the surface of the chip 20 composing the device.

Further embodiments, also included in the invention, can be made by arranging the above-mentioned members of the device in any combination on either side of the chip 20.

The device 1 according to the invention, in all the embodiments and related variations illustrated above, is configured to detect pressures ranging over a wide interval. This wide range is the range permitted by the above-mentioned physical phenomena, on which the device is based, and enabled by the miniaturized dimensions of the sensor members. This range can be, according to a non-limiting example, from $10^{-5}$ mbar to $10^5$ mbar (thus, only excluding extremely low pressure or high vacuum values)

According to a preferred embodiment, the device 1 is configured to detect pressure values between $10^{-4}$ mbar and $10^4$ mbar.

A method for pressure measurement, carried out by means of a device according to the invention, will be now described.

The method comprises the steps of detecting a first pressure value $P_1$ and generating a first electrical signal $S_1$ representative of the first pressure value $P_1$, by at least one first electro-mechanical miniaturized pressure sensor member 11 of the device 1; similarly, detecting a second pressure value $P_2$ and generating a second electrical signal $S_2$ representative of the second pressure value $P_2$, by at least one second miniaturized electro-mechanical sensor member 12 of the device 1, arranged within a respective casing 13 that is suitable to seal it.

The method then comprises the step of determining, by the electronic processing means 10, a measured pressure value P based on the above-mentioned first and second electrical signals, $S_1$ and $S_2$; and finally providing in output the measured pressure value P, by interface means 15 of the device 1.

The first 11 and second 12 sensor members, the electronic processing means 10 and the interface means 15 are all comprised in a single integrated device.

According to an exemplary embodiment, the method further comprises the steps of storing, in the electronic processing means 10, characterization data of the second sensor member 12, at a reference pressure $P_2$; keeping the second sensor member 12 at the reference pressure $P_2$, inside the casing 13; calibrating the first sensor member 11 and the second sensor member 12, by the electronic processing means 10, based on the second electrical signal $S_2$ and on the above-mentioned characterization data.

According to a further exemplary embodiment, the method further comprises the steps of arranging the same pressure in the first 11 and second 12 sensor members; comparing the first $S_1$ and second electrical signal $S_2$ generated thereby; operating a diagnostic procedure of the operation of the first sensor member 11.

According to a still further exemplary embodiment, in the case the diagnostic procedure yields a negative outcome, the method comprises the further step of heating in a controlled way the first sensor member 11, to carry out a degassing and/or a removal of gases adsorbed therein.

As it can be seen, the object of the present invention is achieved by the system described above, by virtue of the illustrated characteristics.

In fact, from what has been described above, it is apparent that the device of the present invention is a miniaturized device capable of providing high precision and reliability performance.

Moreover, the device, due to the structural and functional characteristics described above, results to be self-contained (capable of self-calibration and self-diagnostic). It is also able to deal with, and to correct to a certain extent, the several degradation causes which may actually happen and which would worsen the device performance, by affecting the first sensor member.

Furthermore, the device allows, as illustrated above, to manage microscopic signals at microscopic level, with the consequent further advantage to enhance the achievable signal-to-noise ratios.

To the embodiments of the electro-mechanical miniaturized device for pressure measurements described above, those skilled in the art, in order to meet contingent needs, can carry out modifications, adaptations and replacements of elements with others functionally equivalent also in conjunction with the prior art, also by creating hybrid implementations, without departing from scope of the following claims. Each of the characteristics described as belonging to a possible embodiment can be carried out independently of the other embodiments described herein. It should be also noted that the term "comprising" does not exclude other elements or steps, the term "a" does not exclude a plurality. Furthermore, the figures are not necessarily in scale; on the contrary, relevance is given to the illustration of the principles of the present invention.

The invention claimed is:

1. An electro-mechanical miniaturized device for pressure measurements, comprising:
   at least one first electro-mechanical miniaturized pressure sensor member configured to detect a respective first pressure value (P1) and to generate a first electrical signal (S1) representative of said first pressure value (P1);
   at least one second electro-mechanical miniaturized pressure sensor member, arranged within a respective casing that is suitable to seal the second sensor member, and configured to detect a respective second pressure value (P2) and to generate a second electrical signal (S2) representative of said second pressure value (P2), wherein said respective casing is configured to take a closed state, in which it protects the at least one second sensor member against direct exposure to a surrounding environment, and an open state, in which it allows the at least one second sensor member to be directly exposed to the surrounding environment;
   a hardware processor, operatively connected to the first and the second sensor members, configured to determine a measured pressure value (P) based on said first (Si) and second (S2) electrical signals;
   an interface, operatively connected to the hardware processor and configured to provide an output of said measured pressure value (P),
   wherein said first and second sensor members, the hardware processor, and interface are comprised in a single integrated device.

2. The device according to claim 1, wherein said first and second sensor members, the hardware processor and the interface are comprised in a single chip of the integrated device.

3. The device according to claim 2, wherein said first and second sensor members and the hardware processor are arranged on the same side of the chip composing the device,
   or wherein said first sensor member is arranged on an opposite side of the chip, with respect to said second sensor member and electronic processing means,
   or wherein said first and second sensor members and the hardware processor are arranged so as to project as a relief, on different planes, with respect to the surface of the chip composing the device.

4. The device according to claim 1, wherein each of said first and second sensor members is configured to have a mechanical or electro-mechanical behaviour, related to at least one respective first or second mechanical or electro-mechanical variable, depending on the pressure or on fluid-dynamics to which it is subjected,
   and wherein each of said first (S1) or second (S2) electrical signals is generated based on said at least one respective first or second mechanical or electro-mechanical variable, respectively.

5. The device according to claim 1, wherein each of said first and second sensor members comprises a respective MEMS/NEMS-type oscillating member.

6. The device according to claim 5, wherein each of said MEMS/NEMS-type oscillating members comprises a micro-cantilever, configured to oscillate with a dynamic response that depends on the pressure to which it is subjected.

7. The device according to claim 1, comprising a plurality of second pressure sensor members, to detect a respective plurality of second pressure values (P2), and to generate a respective plurality of second electrical signals (S2) representative of said second pressure values (P2);
   and wherein the hardware processor are further configured to generate the measured pressure value (P) based on a processing of said second electrical signals (S2).

8. The device according to claim 1, wherein said casing is configured to take a closed state, in which it protects the at least one second sensor member against a direct exposure to the surrounding environment, keeping it at a reference pressure coincident with the second pressure value (P2),
   wherein the hardware processor comprise a memory, configured to store characterization data characterizing the second sensor member at the reference pressure (P2),
   and wherein the hardware processor are configured to calibrate the first and the second sensor members based on the second electrical signal (S2) and the stored characterization data.

9. The device according to claim 1, wherein the hardware processor are configured to process data received by the first and the second sensor members, and to carry out a diagnostic procedure of the first sensor member, based on the received data, so as to identify possible hysteresis phenomena and/or imperfections and/or possible thermal and/or mechanical drifts to which the first sensor member may be subjected.

10. The device according to claim 9, wherein the hardware processor are configured to carry out, in case the diagnostic procedure yields a negative outcome, an adjustment and/or compensation and/or optimization procedure of the first sensor member to correct and/or compensate hysteresis phenomena and/or imperfections and/or drifts that are identified based on the results of said diagnostic procedure.

11. The device according to claim 9, further comprising:
    a temperature sensor that detects a temperature;
    a heat supply; and a supply and management circuit coupled to the heat supply configured to carry out a degassing and/or a removal of gases adsorbed on surfaces of the first sensor member, under the control of the hardware processor, and wherein said adjustment procedure of the first sensor member comprises said degassing and/or removal of gases adsorbed on the first sensor member, operating based on the detection of temperature by the temperature sensor.

12. The device according to claim 1, further comprising protection thin films, configured to reduce the adsorption of processing gases and to prevent corrosion phenomena, and arranged so as to cover at least the first sensor member,
or further comprising a package comprising micrometer frame filters, arranged so as to cover at least the sensor members comprised in the device.

13. The device according to claim 1, configured to detect pressure values ranging between $10^{-4}$ mbar and $10^4$ mbar.

14. A method for measuring pressure, carried out by an electro-mechanical miniaturized device, the method comprising the steps of:
detecting a first pressure value (P1) and generating a first electrical signal (S1) representative of the first pressure value (P1), by at least one first electro-mechanical miniaturized pressure sensor member of the device;
detecting a second pressure value (P2) and generating a second electrical signal (S2) representative of the second pressure value (P2), by at least one second electro-mechanical miniaturized pressure sensor member of the device, arranged within a respective casing that is suitable to seal it,
wherein said respective casing is configured to take a closed state, in which it protects the at least one second sensor member against direct exposure to a surrounding environment, and an open state, in which it allows the at least one second sensor member to be directly exposed to the surrounding environment;
determining a measured pressure value (P) based on said first (Si) and second (S2) electrical signals, by a hardware processor of the device;
providing an output of the measured pressure value (P), by an interface of the device,
wherein said first and second sensor members, the hardware processor, and the interface are comprised in a single integrated device.

15. The method according to claim 14, further comprising the steps of:
storing, in the hardware processor, characterization data of the second sensor member, at a reference pressure (P2);
keeping the second sensor member at the reference pressure (P2), within the casing;
calibrating the first sensor member and the second sensor member, by the hardware processor, based on the second electrical signal (S2) and on said characterization data.

* * * * *